United States Patent [19]
Day

[11] Patent Number: 5,932,221
[45] Date of Patent: Aug. 3, 1999

[54] GENISTIN-ENRICHED FRACTION FROM SOY MEAL

[76] Inventor: Charles E. Day, 1434 Sunbeam Rd., Leitchfield, Ky. 42754

[21] Appl. No.: 09/182,067

[22] Filed: Oct. 29, 1998

Related U.S. Application Data

[60] Provisional application No. 60/064,364, Oct. 30, 1997.
[51] Int. Cl.⁶ .................................................. A61K 35/78
[52] U.S. Cl. ....................... 424/195.1; 514/455; 514/456; 514/457
[58] Field of Search .............................. 424/195.1; 426/2, 426/629, 648; 514/455, 456, 457, 874, 899

[56] References Cited

U.S. PATENT DOCUMENTS

| | | | |
|---|---|---|---|
| 5,424,331 | 6/1995 | Shlyankevich | 514/456 |
| 5,506,211 | 4/1996 | Barnes et al. | 514/27 |
| 5,554,519 | 9/1996 | Weber et al. | 435/125 |
| 5,569,459 | 10/1996 | Shlyankevich | 424/195.1 |
| 5,637,562 | 6/1997 | Shen et al. | 514/2 |
| 5,670,632 | 9/1997 | Chaihorsky | 536/8 |
| 5,679,806 | 10/1997 | Zheng et al. | 549/403 |
| 5,702,752 | 12/1997 | Gugger et al. | 426/634 |

OTHER PUBLICATIONS

Walter, "Genistin and Its Aglucone Genitein", Journ. Amer. Chem. Soc., 63:3273–3276, Dec. 1941.

Brady, J., Solubility & Temp., "Fractional Crystallization", Gen. Chem. Prin. & Struct., 2nd ed.;263–266, 1975.

Messina, M. and Stephen Barnes, "The Role of Soy Products in Reducing Risk of Cancer", Journ. Natl. Cancer Instit. 83:541–545, Apr. 1991.

Peterson, G. and Stephen Barnes, "Genisteinand Biochanin A Inhibit the Growth of Human Prostate Cancer Cells but Not Epidermal Growth Factor Receptor Tyrosine Autophosphorylation", The Prostate 22:335–345, Jan. 1993.

Anthony, M. et al, "Plant and Mammmalian Estrogen Effects on Plasma Lipids of Female Monkeys", Circulation 90: Suppl.:I–235 (abstract), Oct. 1994.

Anthony, M. et al, "Effects of Soy Protein Photoestrogens on Cardiovcascular Risk Factors in Rhesus Monkeys", Journ. Nutrit. 125:Suppl: 3S:803S–804S(abstract), 1995.

Anthony, M. et al, "Does Soy Supplementation Improve Corornary Heart Disease?", Circulation 91:925 (abstract), Feb. 1995.

*Primary Examiner*—Jean C. Witz
*Assistant Examiner*—Angela N. Trafton

[57] ABSTRACT

Disclosed is how to make and to use a genistin-enriched fraction from soy meal. The fraction is prepared by acetone extraction of soy meal, followed by ice-water precipitation. The resulting composition is useful as a pharmaceutical or a dietary supplement for the treatment or prevention of cancer, cardiovascular disease, osteoporosis, or adverse symptoms of menopause in a human.

2 Claims, No Drawings

GENISTIN-ENRICHED FRACTION FROM SOY MEAL

CROSS-REFERENCE TO RELATED APPLICATIONS

This application incorporates by reference the applicant's U.S. Provisional application Ser. No. 60/064,364, filed Oct. 30, 1997, from which priority is claimed.

FIELD OF THE INVENTION

The invention relates to a composition prepared from soy meal that is useful as a pharmaceutical or a dietary supplement.

DESCRIPTION OF THE RELATED ART

Bulk soy meal, the product of the pulverization and hexane extraction of soybeans, is among the world's most readily available and heavily traded bulk commodities. The glycoside genistin, found in soybeans, is metabolized to the pharmaceutically active aglycone genistein when administered to humans. Genistein possesses a myriad of important potential therapeutic effects, including antioxidant, anticancer, and anti-osteoporosis activities (for which see U.S. Pat. No. 5,498,631).

There are processes for obtaining genistin-enriched fractions from soybeans known in the art. However, these processes either use soybeans rather than soy meal as the starting material (U.S. Pat. No. 5,141,746) or else incorporate a multiplicity of separations (U.S. Pat. Nos. 5,702,752 and 5,792,503) and/or transformations (U.S. Pat. Nos. 5,637,561, 5,637,562 and 5,763,389). None makes primary use of the readily available solvent acetone.

There has been a need in the art for a process by which a genistin-enriched fraction can be prepared from readily available bulk soy meal and which does not involve multiple complex separations.

BRIEF SUMMARY OF THE INVENTION

A genistin-enriched fraction is prepared from soy meal by acetone extraction followed by ice-water precipitation. The process by which the fraction is prepared meets the need hitherto unmet in the art for a simple scheme by which a genistin-enriched fraction can be prepared directly from a bulk commodity, using readily available solvents, and not involving complicated separations. The composition is useful as a pharmaceutical or a dietary supplement for the treatment or prevention of cancer, cardiovascular disease, osteoporosis, or adverse symptoms of menopause in a human.

DETAILED DESCRIPTION OF THE INVENTION

In order to prepare a distinctive isoflavone-enriched fraction, that is particularly enriched in genistin, from soybeans, I performed an acetone extraction of soy meal. The soy isoflavones are generally soluble in acetone, while soy phosphatidylcholine is generally insoluble in acetone, so the resultant acetone extract of soy meal is a fraction relatively enriched in isoflavones and depleted of phosphatidylcholine. I then performed an ice-water precipitation of the acetone extract. One of the principal soy isoflavones, daidzin, is soluble in ice-water, whereas the isoflavone I wished in particular to retain, i.e. genistin, is insoluble in ice-water. Therefore the ice-water precipitate of the acetone extract was relatively depleted of daidzin and enriched in genistin. I refer to said precipitate below as "the isoflavone-enriched fraction that is particularly enriched in genistin."

As an example, one gram of soy meal is mixed with 10 mL acetone to form a slurry. The slurry is then agitated vigorously and the solids are allowed to settle. The greater part of the solvent is then evaporated. To the remaining volume is added at least five, but preferably between ten and twenty, volumes of ice-cold water. After the addition of water the resultant mixture is sedimented by centrifugation. The isoflavone-enriched fraction that is particularly enriched in genistin is concentrated in the sedimented precipitate.

Liquid chromatographic analysis of the isoflavone-enriched fraction that is particularly enriched in genistin confirmed that the glycosides genistin and daidzin were among its principal components.

The isoflavone-enriched fraction that is particularly enriched in genistin is useful as a dietary supplement for the prevention or treatment of any of the following conditions: cancer, cardiovascular disease, osteoporosis, and adverse symptoms of menopause.

The isoflavone-enriched fraction that is particularly enriched in genistin is also useful as a pharmaceutical for the prevention or treatment of any of the following conditions: cancer, cardiovascular disease, osteoporosis, and adverse symptoms of menopause.

As an example, a pharmaceutical formulation comprising the isoflavone-enriched fraction that is particularly enriched in genistin is administered to a human patient diagnosed with breast cancer, prostate cancer, cardiovascular disease, or osteoporosis, such patient being in need of treatment for that same condition.

As another example, a nutritional supplement comprising the isoflavone-enriched fraction that is particularly enriched in genistin is ingested by a human desirous of decreasing his or her risk of breast cancer, cardiovascular disease, osteoporosis, or prostate cancer.

As yet another example, a pharmaceutical formulation or nutritional supplement comprising the isoflavone-enriched fraction that is particularly enriched in genistin is taken by a menopausal or postmenopausal human female for mitigation of adverse symptoms of menopause, such symptoms comprising hot flashes, hypercholesterolemia, or osteoporosis.

As a final example, one dose per day of a pharmaceutical formulation or nutritional supplement comprising the isoflavone-enriched fraction that is particularly enriched in genistin, in dosage form such that said formulation or supplement contains about 75 mg genistin per dose, is taken by a menopausal or postmenopausal human female for mitigation of adverse symptoms of menopause, such symptoms comprising hot flashes, hypercholesterolemia, or osteoporosis.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can legally be accorded to the appended claims.

I claim:

1. A method for producing a genistin-containing composition comprising:

(a) extracting of soy meal with acetone to form an acetone extract;

(b) mixing of ice-cold water with said acetone extract to form a precipitating mixture; and (c) collecting of the precipitating mixture.

2. A method of producing a genistin-containing composition comprising:

(a) extracting of soy meal with acetone to form an acetone extract;

(b) concentrating of said acetone extract by evaporation of a portion of the supernatant solvent of said acetone extract to form one volume of concentrated acetone extract;

(c) mixing of at least five volumes of ice-cold water with said one volume of concentrated acetone extract to form a precipitating mixture.

* * * * *